United States Patent [19]
Jarrett et al.

[11] Patent Number: 5,342,395
[45] Date of Patent: * Aug. 30, 1994

[54] ABSORBABLE SURGICAL REPAIR DEVICES

[75] Inventors: Peter K. Jarrett, Southbury, Conn.; Donald J. Casey, Mars, Pa.; Louis Rosati, Norwalk, Conn.

[73] Assignee: American Cyanamid Co., Wayne, N.J.

[*] Notice: The portion of the term of this patent subsequent to Jan. 14, 2009 has been disclaimed.

[21] Appl. No.: 819,701

[22] Filed: Jan. 13, 1992

Related U.S. Application Data

[63] Continuation-in-part of Ser. No. 799,521, Nov. 27, 1991, which is a continuation-in-part of Ser. No. 548,802, Jul. 6, 1990, Pat. No. 5,080,665.

[51] Int. Cl.⁵ .................. C08J 3/10; A61B 17/00
[52] U.S. Cl. ...................... 606/219; 524/411; 524/415; 524/450; 524/462; 528/354; 606/76
[58] Field of Search .................. 606/69–71, 606/76; 524/381, 411, 413, 415, 450, 462; 528/354, 359, 361; 428/395; 523/105, 113

[56] References Cited

U.S. PATENT DOCUMENTS

| | | | |
|---|---|---|---|
| 3,301,824 | 1/1967 | Hostettler et al. | 260/77.5 |
| 3,639,503 | 2/1972 | Matzner | 260/860 |
| 4,045,418 | 8/1977 | Sinclair | 260/78.3 |
| 4,052,988 | 10/1977 | Doddi et al. | 128/335.5 |
| 4,057,537 | 11/1977 | Sinclair | 260/78.3 |
| 4,243,775 | 1/1981 | Rosensaft et al. | 525/415 |
| 4,279,249 | 7/1981 | Vert et al. | 128/92 |
| 4,300,565 | 11/1981 | Rosensaft et al. | 128/335.5 |
| 4,429,080 | 1/1984 | Casey et al. | 525/415 |
| 4,539,981 | 9/1985 | Tunc | 606/77 |
| 4,595,713 | 6/1976 | St. John | 523/105 |
| 4,643,734 | 2/1987 | Lin | 623/16 |
| 4,700,704 | 10/1987 | Jamiolkowski | 128/335.5 |
| 4,705,820 | 11/1987 | Wang et al. | 524/381 |
| 4,788,979 | 12/1988 | Jarrett et al. | 128/335.5 |
| 4,891,263 | 1/1990 | Kotliar et al. | 428/225 |
| 4,905,680 | 3/1990 | Tunc | 606/77 |
| 4,916,193 | 4/1990 | Tang et al. | 525/413 |
| 4,920,203 | 4/1990 | Tang et al. | 525/409 |

FOREIGN PATENT DOCUMENTS

| | | |
|---|---|---|
| 808731 | 3/1969 | Canada . |
| 1056055 | 3/1989 | Japan . |
| 02084431 | 3/1990 | Japan . |
| WO90/12550 | 11/1990 | PCT Int'l Appl. . |

OTHER PUBLICATIONS

Macromolecules vol. 17, No. 12 1984 pp. 2764–2767 – Synthesis of ABA Triblock Copolymers of e-Caprolactone and DL-Lactide by C. X. Song & X. D. Feng.

Block Copolymers of L-Lactide, D-Lactide & E-Caprolactone P. J. Dijkstra, A. Bulte and J. Feijen – 17th Annual Meeting of Society for Biomaterials May 1–May 5, 1991 p. 184.

Storz Instruments for Maxiliofacial Surgery Part of 1988 Brochure – Storz Surgical Specialties, St. Louis, Mo. USA.

Journal of Polymer Science: Polymer Letters Edition, vol. 21, pp. 593–600 (1983 John Wiley & Sons, Inc.) Synthesis & Evaluation of Biodegradable Block Copolymers of e-Caprolactone and DL-Lactide.

*Primary Examiner*—Stephen C. Pellegrino
*Assistant Examiner*—Gary Jackson
*Attorney, Agent, or Firm*—C. F. Costello, Jr.

[57] ABSTRACT

A load-bearing, bioabsorbable surgical repair device manufactured from a copolymer having a plurality of first linkages of lactide or lactide/glycolide, and a plurality of second linkages of a polymer having a glass transition temperature below ambient temperature. The second linkages preferably are selected from: 1,3-dioxan-2-one; 1,4-dioxan-2-one; and ε-caprolactone.

9 Claims, 3 Drawing Sheets

ABSORBABLE SURGICAL REPAIR DEVICES

CROSS REFERENCES

This is a continuation-in-part application of U.S. Ser. No. 07/799,521 filed Nov. 27, 1991, which is a continuation-in-part application of U.S. Ser. No. 07/548,802 filed Jul. 6, 1990, now U.S. Pat. No. 5,080,665, both of which are incorporated herein by reference.

FIELD OF THE INVENTION

This invention relates to absorbable surgical repair devices having a combination of hard and soft phases, and more particularly to deformable devices formed of a hard phase of lactic acid ester linkages or a combination of lactic acid ester linkages and glycolic acid ester linkages, and a soft phase of a polymer having a glass transition temperature below ambient temperature.

BACKGROUND OF THE INVENTION

There is a need for surgical repair devices such as bone plates, screws, staples, and other tissue and fracture fixation devices which are bioabsorbable. Suitable polymeric materials are desired which are readily and safely absorbed by the body, a process also known as bioresorption, at a rate which enables the repair device to maintain sufficient integrity while the soft tissue or bone heals. Surgical repair devices formed of materials which are absorbed too quickly may fail when compressive, tensile or flexural loads are placed on the devices before the tissue or bone has fully healed.

There is also a need for absorbable polymeric materials that can be permanently deformed at room or body temperature, especially in medical device applications that require the material to be reshapable. One such application is in absorbable maxillofacial bone fixation plates where complex fracture site surface contours are often encountered. For comparison, see the Masterpiece ™ maxillofacial bone plate system (Storz Instrument Co., Mo. 63122, USA). Another application is in absorbable surgical clips and staples where improved toughness and ductility are desirable.

As the term is used herein, permanent deformation refers to a type of deformation wherein the material does not completely return to its original form once the deforming load is removed. Such a deformation results from the properties of ductility or plasticity. Ductility and plasticity have equivalent meanings as used in describing the invention and can be applied in elongational or flexural deformations. A ductile polymer "yields" when a sufficient stress or strain are applied. The yielding process can involve molecular reorganization (usually in softer polymers with glass transition temperatures below ambient temperature) or crazing (usually in more rigid polymers with glass transition temperatures higher than ambient temperature), discussed in more detail below.

The following U.S. patents are pertinent to the present inventions described in this application: 4,243,775, 4,279,249, 4,300,565, 4,539,981, 4,550,449, 4,744,365, 4,788,979, 4,839,130, 4,844,854. Also pertinent is the international patent application WO 89/05664 and corresponding U.S. Pat. Nos. 4,891,263, 4,916,193, 4,916,207 and 4,920,203. These patents and the application are incorporated herein by reference.

The modification of glassy polymeric materials for improved toughness is well known in the non-absorbable polymer art. Perhaps the most notable example of a toughened glassy plastic is high impact polystyrene (HIPS). The following review article describes the property improvements of HIPS: Soderquist, M. E. and Dion, R. P., "High Impact Polystyrene," in *Encyclopedia of Polymer Science and Engineering*, Vol. 16, pp. 88'97, John Wiley & Sons, New York, 1989. Many other nonabsorbable polymers have been modified for improved toughness or impact resistance. A general review of this field can be found in Yee, A. F., "Impact Resistant Materials," in *Encyclopedia of Polymer Science and Engineering*, Vol. 8, pp. 59-68, John Wiley & Sons, New York, 1989 and in Bucknail, C. B., *Toughened Plastics*, Applied Science Publishers, London, 1977 and in *Comprehensive Polymer Science*, Vol. 2, section 15.3, pp. 526-532, C. Booth & C. Price, eds., Pergamon Press, New York, 1989. Generally, toughness and impact resistance have been improved by incorporating a discontinuous rubbery phase in the parent polymer matrix. This has been done by physical blending or by preparation of block or graft copolymers. Similar concepts have been applied to thermosets such as epoxy resins (see Yee, A. F. and Pearson, R. A., "Toughening Mechanisms in Elastomer-Modified Epoxies Part 1 Mechanical Studies," J. Mat. Sci., Vol. 21, 1986, pp. 2462-2474 and Pearson, R. A. and Yee, A. F., "Toughening Mechanisms in Elastomer-Modified Epoxies Part 2 Microscopy Studies," J. Mat. Sci., Vol. 21, 1986, pp. 2475-2488. All of the above cited disclosures are incorporated herein by reference. Although increases of ductility in nonabsorbable rubber modified plastics have been reported, the primary purpose of the modification has been to impart impact resistance and toughness. To our knowledge this property modification method has not been put to use in medical devices, either absorbable or nonabsorbable.

The U.S. Pat. Nos. 4,243,775 and 4,300,565 cited above disclose absorbable polymeric compositions which were thought to form a two phase morphology. These patents do not mention any enhancement of deformability in bending due to the presence of a rubbery phase.

Some other patents (U.S. Pat. Nos. 4,744,365, 4,839,130 and 4,844,854) disclose two phase copolymers of lactide and glycolide. These patents do not mention any enhancement of deformability in bending other than reduced brittleness. Also, the copolymers disclosed in the '365, '130 and '854 patents do not contain a rubbery phase; rather, they contain two semicrystalline glassy phases. The utility of these two phase copolymers are described as a surgical clip or staple. The rubber toughened materials of this application may also be useful as a surgical clip or staple.

None of the prior art mentions the usefulness as a medical device of materials which can be permanently deformed at room temperature through crazing. The term "crazing" is used in its typical meaning of cavitation and/or microcrack formation, such as occurs during bending one portion of a suitable material relative to a second portion to form crazes at the bend site. Crazing will not occur if the material is too rubbery or too brittle. In some materials, sufficient crazing can take place to permit the material to deform ductily or plastically under an applied load.

U.S. Pat. No. 4,279,249 claims bioabsorbable boneplate devices manufactured from a copolymer of at least 90% units derived from lactic acid and reinforcing fibers made of polyglycolic acid or a copolymer thereof.

Nowhere in this patent is it disclosed that the material can be permanently deformed by bending at room temperature, although improved resilience and shock resistance are disclosed. Also, this patent claims a "matrix" polymer of at least 90% lactic acid units.

Other bioabsorbable bone fixation devices have been fashioned from high molecular weight poly(1-lactide); see, e.g. U.S. Pat. Nos. 4,539,981 and 4,550,449. This material does not allow reshaping at room temperature and no mention of such a property is made in these patents.

Block copolymers containing trimethylene carbonate and lactide were exemplified in the U.S. Pat. No. 4,916,193. The materials exemplified were higher in rubber phase content compared to the compositions described in this application. In this patent no mention was made of ductile properties or the usefulness of such a property in medical devices.

Block copolymers containing trimethylene carbonate, caprolactone, and glycolide as well as block copolymers containing caprolactone and glycolide were exemplified for use as suture coatings in U.S. Pat. No. 4,788,979. In contrast to the materials of the present invention, these materials were also rich in soft phase forming units. No mention was made of ductile properties in this patent.

SUMMARY OF THE INVENTION

It is therefore an object of the present invention to provide an improved surgical repair device which is bioabsorbable.

Yet another object of this invention is to provide such a surgical repair device which is capable of bearing compressive, tensile and/or flexural loads without failure over its intended useful life.

A further object of this invention is to provide such a surgical repair device which can be deformed at room temperature.

The present invention describes medical devices made from a copolymer which is composed of first, hard phase linkages of lactic acid ester (lactide) or a lactide/glycolide copolymer and second, soft phase linkages of a rubbery polymer or copolymer with a low glass transition temperature such as caprolactone, trimethylene carbonate or p-dioxanone, or copolymers thereof. The predominance (preferably more than 50%) of the hard phase provides sufficient rigidity and therefore mechanical stability. The rubbery or soft block imparts the deformability in bending to the surgical repair devices described in this application.

This invention also relates generally to absorbable polymeric materials possessing an enhanced ability for permanent deformation at room or body temperature. This invention relates further to the use of these materials in medical device applications that require the material to be reshapable. Applications where these materials are believed to be useful include the following:
1. Absorbable maxillofacial bone fixation plates.
2. Absorbable bone screws or other fastening devices such as suture anchors.
3. Absorbable surgical clips and staples.
4. Absorbable bone fixation rods and screws.
5. Absorbable sutures.

BRIEF DESCRIPTION OF THE DRAWINGS

Other objects, features and advantages will occur from the following description of preferred embodiments and the accompanying drawings, in which.

DETAILED DESCRIPTION OF INVENTION

Figure 1:
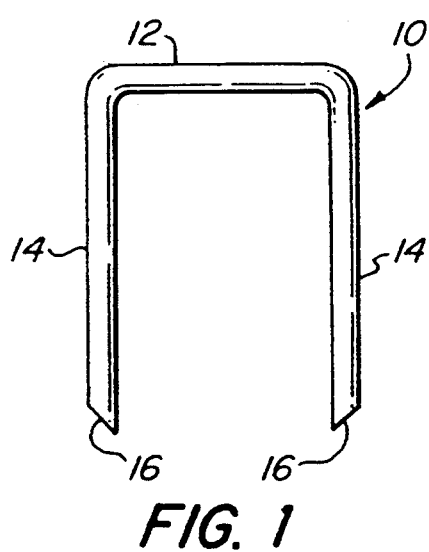
FIGS. 1 and 2 are side views of a preformed and deformed staple, respectively, according to the present invention.

This invention may be accomplished by manufacturing a surgical repair device from a copolymer having a combination of hard and soft phases. The hard phase comprises lactic acid ester (lactide) linkages or a combination of lactic acid ester linkages and glycolic acid ester (glycolide) linkages, and the soft phase is a low glass transition temperature polymer such as polymer E-caprolactone. Both the hard and soft phase polymers are bioabsorbable, and together provide an absorbable copolymer.

The hard phase polymer preferably has a glass transition temperature above ambient temperature and the soft phase polymer preferably has a glass transition temperature below ambient temperatures. The term "ambient temperature" refers to the body temperature of a patient into which the repair device is intended to be implanted, or the room temperature at which the repair device is intended to be deformed.

A surgical repair device according to the present invention is capable of bearing a compressive, tensile and/or flexural load during implantation and/or after implantation in the body of a patient. Examples of such devices with preferred dimensions are as follows:
 A. Plates
  1. Lengths: 10 to 200 mm
  2. Thicknesses: 0.5 to 6.0 mm
  3. Widths: 1.5 to 20 mm
 B. Screws
  1. Thread Diameters: 1.0 to 7.0 mm
  2. Core Diameters: 0.75 to 3.5 mm
  3. Overall Lengths: 2 to 120 mm
  4. Thread Lengths: 1 to 110 mm
 C. Intramedullary Nails
  1. Diameters: 8 to 20 mm
  2. Lengths: 200 to 500 mm
 D. Fracture Fixation Rods
  1. Diameter: 1.5 to 4.5 mm
  2. Lengths: 25 to 70 mm
 E. Suture Anchoring Devices
  1. Outer Diameter: 1.5 to 5.5 mm
  2. Overall Length 3.5 to 10.5 mm The size of the suture anchoring device is dependent on the intended application. The larger anchors would be used in larger bones (shoulder, knee) where high pull-out strength is required. The smaller anchors could be implanted in bones when less pull-out force is required and/or bone size (e.g. in the hand or foot) is relatively small.
 F. Soft Tissue to Bone Fixators
  1. Outer Head Diameter: 5.5 to 8.5 mm
  2. Overall Device Length: 10 to 50 mm
 G. Staples and Clips Examples of staples are provided below and in the cross-referenced applications which are incorporated herein by reference.

The above devices can be formed by heating a copolymer according to the invention to a liquid state, and forcing the liquified polymer into a mold cavity having a geometry corresponding to the shape of the desired device. The copolymer can be used by itself, or together with another material such as glass fibers or other fiber reinforcement to enhance strength properties.

Alternatively, a composite or matrix can be formed by melting the copolymer or dissolving the copolymer in a solution, and forming a fine fiber or wire which is wound on a spool. The fiber or wire can then be wound, braided, woven, knitted or otherwise joined to form a desired 3-dimensional shape. The surgical repair device can be established by a plurality of layers of a single strand of the copolymer, or by a woven, knitted or braided matrix of a plurality of strands of the copolymer. In another construction, the surgical repair device has a non-woven, felt-like structure. In yet another construction, the fiber or wire is wound about a core material, which preferably is also bioabsorbable, until the desired shape is achieved. Once a desired thickness and composition is achieved, with or without fillers, the structure in some constructions is heated to fuse the copolymer fibers into a solid device.

Molded, non-oriented material is preferred for solid bone plates, in which the copolymer preferably contains 50–95 mole percent of the hard phase, more preferably 55–90 mole percent and most preferably 60–85 mole percent. A block copolymer is preferred in this application. If deformability is desired, at least 5% E-caprolactone, trimethylene carbonate or p-dioxanone is preferred. Deformability is greatly enhanced by having about 15–40 mole percent of these soft-phase polymers while retaining desirable stiffness.

In other applications, such as for sutures and staples, an oriented material is desired. Deformability of a device formed from an oriented material is due primarily to a ductile, yielding behavior instead of crazing. Deformability by crazing occurs primarily in unoriented materials such as the above-described use in bone plates.

A composition of 95% lactide and 5% soft phase polymer is preferred for oriented materials. The soft phase polymer is believed to exert noticeable effects in amounts as low as 1 or 2%.

A block copolymer provides an overall higher glass transition temperature, although for concentrations of less than 5% of soft phase polymer, any difference among block, graft, and random copolymers becomes far less noticeable. The number of units within each block is preferred to be greater than 25, and more preferably is greater or equal to 50 repeating units.

Although not specifically exemplified, it is recognized that a number of materials could be envisioned which could possess similar properties to the exemplified copolymers. To have similar properties, it is necessary that the material have a continuous "hard" phase and a "soft" phase. The term "continuous phase" as used herein describes a phase that extends in some manner throughout the continuum of the material without interruption or break. It is preferred that the soft phase be discontinuous, although this is not required. To form separate hard and soft phases, the hard and soft species must not be fully miscible in their final polymeric form. The final polymeric form could be a block or graft copolymer or a blend of homopolymers and/or copolymers. Alternatively, con-trolled blending methods could be employed with otherwise miscible polymers to minimize phase mixing in the final article. The following is a list of possible alternative materials which are included in this invention:

1. Block copolymers forming "hard" and "soft" phases
   A. Hard phase forming monomers
      1. l-Lactide, d-lactide or meso-lactide
      2. dl-Lactide, variable ratios of d to l
      3. Mixtures of glycolide and lactide
      4. Other monomers or mixtures of monomers that form absorbable polymers with glass transition temperatures above room temperature.
   B. Soft phase forming monomers or polymers
      1. E-Caprolactone (2-oxepanone or oxepan-2--one)
      2. Trimethylene carbonate (1,3-dioxan-2-one)
      3. p-Dioxanone (1,4-dioxan-2-one)
      4. Poly(alkylene oxides)
      5. Poly(alkylene diglycolates)
      6. Mixtures of 1,2 or 3 above
      7. Other monomers or mixtures of monomers that form absorbable polymers with glass transition temperatures below room temperature.

Blends of "hard" and "soft" absorbable polymers
   A. Hard phase forming polymers
      1. Poly(l-lactide), poly(d-lactide) or poly (mesolactide)
      2. Copolymers of l-lactide, d-lactide or meso-lactide
      3. Lactide-glycolide copolymers
      4. Other polymers or copolymers with glass transition temperatures above room temperature.
   B. Soft phase forming polymers
      1. Poly (E-caprolactone)
      2. Poly (trimethylene carbonate)
      3. Poly (p-dioxanone)
      4. Poly(alkylene oxides)
      5. Poly(alkylene diglycolates)
      6. Copolymers of 1, 2, or 3 above
      7. Other polymers or copolymers with glass transition temperatures below room temperature.

The selection of a preferred material will depend on the desired physical properties of the final article. The preferred material will also be determined by the desired in vivo degradation and absorption rates. Several variables can be adjusted to obtain the desired properties. Absorption rate is known to be affected by composition and crystallinity. For example a hard phase of poly(l-lactide) would provide a slow degradation rate due to its hydrophobic, crystalline nature, whereas a copolymer of glycolide and dl-lactide in equal amounts would provide a fast degradation rate due to its more hydrophilic, noncrystalline nature. The presence of up to twenty weight percent of glycolide in the hard phase, the remainder of the hard phase being l-lactide, increases bioabsorption without substantially diminishing the mechanical strength imparted by the lactide.

If increased stiffness or strength is required, an absorbable fiber or fabric reinforcement can be added to make a composite structure. Further improvement of the composite properties can be made by manipulating the location of the reinforcement within the composite, for example, if the reinforcement is placed in the center plane of a laminated structure, the composite would be expected to be stiffer in tension (forces applied parallel to the plane) than in flexion (forces applied normal to the plane), allowing reshaping by bending.

The invention is further described in the following examples:

EXAMPLE 1: GENERAL POLYMERIZATION PROCEDURE FOR l-LACTIDE-b-ε-CAPROLACTONE COPOLYMERS

ε-Caprolactone (CAP), diethylene glycol (DEG), and stannous octoate were combined and melted under a nitrogen atmosphere. The mixture was charged into a nitrogen purged stirred reactor at 200° C. The contents were stirred at this temperature until maximum melt viscosity was achieved. l-Lactide was melted under a nitrogen atmosphere and charged into the reactor. The contents were maintained at 200° C. until maximum melt viscosity was obtained. The polymer was discharged from the reactor, ground and dried in a vacuum oven for 12–18 hours at 100° C. and 0.2 mm Hg. Specific examples of polymers prepared by this procedure are summarized in Table 1.

EXAMPLE 2-EXTRUDED AND DRAWN MONOFILAMENT FIBERS—EXTRUSION OF l-LACTIDE RICH POLYMERIC WIRES

Fibers of different diameters to be used for test specimen preparation were extruded and drawn in the following manner. The polymer was dried in a vacuum oven prior to being added to the hopper of an extruder with a preheated barrel. It was extruded through a single jet with a diameter of 0.120 inch. The extrudate was quenched in 25° C water at a distance of approximately 3 inches from the jet. The extrudate was then drawn in two stages while the strand was passing through two 4 foot long, circulating hot air ovens. The drawn polymeric wire was collected on a 3.5 inch diameter spool and stored in a dry environment. The specific extrusion conditions for the polymers of Example 1 are shown in Table 2a and their mechanical properties are shown in Table 2b.

All of the fibers listed in Table 2a and 2b were found to undergo ductile deformation when bent at room temperature.

TABLE 1

Poly(Caprolactone-b-1-Lactide)

| | Charged Composition | | | | | | Polymerization Time (Hr:Min) Reaction Stage | | Analyzed Composition | | |
|---|---|---|---|---|---|---|---|---|---|---|---|
| | l-Lac/Cap | | DEG[1] | | Stannous octoate | | | | l-Lac/Cap | | IV |
| Example | (grams) | (mole %) | (mg) | (mole %)[2] | (mg) | (mole %)[2] | 1 | 2 | (mole %)[2] | (Wt. %) | (CHCl₃)[4] |
| 1.a | 201.35/35.00 | 80/20 | 18.1 | 0.01 | 20.7 | 0.003 | 1:03 | 2:07 | 81.9/18.2 | 85.0/15.0 | 1.80 |
| 1.b | 170.38/29.62 | 80/20 | 15.3 | 0.01 | 17.3 | 0.003 | 1:03 | 1:59 | 81.4/18.6 | 84.7/15.3 | 1.76 |
| 1.c | 170.38/29.62 | 80/20 | 15.3 | 0.01 | 17.3 | 0.003 | 0:48 | 2:45 | 80.6/19.4 | 84.0/16.0 | 1.69 |
| 1.d | 170.38/29.62 | 80/20 | 15.3 | 0.01 | 17.3 | 0.003 | 0:48 | 2:50 | 81.1/18.9 | 84.4/15.6 | 1.84 |
| 1.e | 213.75/11.25 | 95/5 | 16.6 | 0.01 | 19.0 | 0.003 | 0:38 | 2:54 | 94.1/5.9 | 95.3/4.7 | 1.74 |
| 1.f | 213.75/11.25 | 95/5 | 16.6 | 0.01 | 19.0 | 0.003 | 0:28 | 3:00 | 93.6/6.4 | 94.5/5.1 | 1.74 |

[1]DEG = Diethylene glycol.
[2]Based on moles of l-Lactide plus Cap.
[3]Determined by [1]H-Nuclear Magnetic Resonance spectroscopy. In all cases residual monomer was <0.5 wt %.
[4]Inherent viscosity, measured in Chloroform at 30° C., polymer concentration = 0.5 g/dL.

TABLE 2a

| Polym. wire sample | Polymer From Example | Final Diameter (mm) | Head Temp. (°C.) | 1st Draw Ratio | 1st Oven Temp (°C.) | 2nd Draw Ratio | 2nd Oven Temp (°C.) |
|---|---|---|---|---|---|---|---|
| 1 | 1.c-d | 0.557 | 215 | 5.68 | 89 | 1.09 | 100 |
| 2 | 1.c-d | 0.467 | 216 | 5.94 | 89 | 1.10 | 99 |
| 3 | 1.c-d | 0.394 | 216 | 5.73 | 90 | 1.10 | 99 |
| 4 | 1.e-f | 0.529 | 217 | 5.29 | 98 | 1.13 | 111 |
| 5 | 1.e-f | 0.484 | 215 | 5.64 | 100 | 1.11 | 113 |
| 6 | 1.e-f | 0.374 | 215 | 5.76 | 100 | 1.11 | 113 |

TABLE 2b

POLYMERIC WIRE MECHANICAL PROPERTIES

| Polym. Wire Sample | Polymer From Example | Diameter (mm) | Modulus (10³ psi) | At Break Strength (10³ psi) | At Break Strain (%) |
|---|---|---|---|---|---|
| 1 | 1.c-d | 0.557 | 821 | 47.8 | 22.6 |
| 2 | 1.c-d | 0.467 | 846 | 53.5 | 21.5 |
| 3 | 1.c-d | 0.394 | 933 | 54.9 | 22.0 |
| 4 | 1.e-f | 0.529 | 1036 | 59.8 | 26.6 |
| 5 | 1.e-f | 0.484 | 1029 | 59.4 | 26.2 |
| 6 | 1.e-f | 0.374 | 1064 | 60.7 | 22.4 |

Dimensional and Mechanical Testing of Polymeric Wires

The diameter, tensile strength, and modulus of the drawn fibers listed in Table 2a were determined in the following manner. The fiber diameter was determined under a specified pressure applied by the presser foot of a gauge. The gauge was of the deadweight type and equipped with a direct-reading dial graduated to 0.002 mm as prescribed by USP XXII 1990 (General Chapters, Physical Tests and Determinations, <861->Sutures—Diameter, pg. 1614). The tensile strength and modulus were determined using an Instron Testing Machine. The mean dimensional measurements and tensile values are reported in Table 2b.

EXAMPLE 3: THERMAL ANALYSIS OF COPOLYMERS AND POLYMERS

Samples of the polymers of Example 1 were analyzed by differential scanning calorimetry (DSC) using a Perkin Elmer DSC-4 instrument. Scanning conditions were from −40° C. to 240° C at 20° C. per minute under nitrogen. Melting points (Tm) and enthalpy of fusion ($\Delta H_f$) values were determined by scanning material that had been annealed at 110° C. for 16 hours. The glass transition temperatures (Tg) were determined after quenching the specimen from the melt following the first scan. Some of the samples exhibited two Tg's in the temperature region scanned: Tg(1) and Tg(2). The presence of two Tg's indicates the sample has two amorphous phases. The results of the thermal analyses are shown in Table 3.

TABLE 3

Thermal Analysis Data

| Polymer From Example | Tg(1) (°C.) | Tg(2) (°C.) | Tm (°C.) | ΔH$_f$ (J/g) | % Cryst.[1] |
|---|---|---|---|---|---|
| 1a | | ca. 60* | 50.4, 173.8 | 5.81, 44.65 | 4.3, 48.1 |
| 1e | | 63.6 | 49.6, 178.1 | 1.34, 55.25 | 1.0, 59.5 |

[1]Calculated crystallinity values based on ΔH$_f$ of 100% crystalline polymer taken from "Polymer Handbook", Third Edition, J Brandup and E. H. Immergut, John Wiley and Sons, 1989.

Lower Tg was below the temperature range tested, but is believed to be about −60° C.

Two melting endotherms were observed. The lower temperature transition is the ε-caprolactone-rich phase melting point and the higher temperature transition is the l-lactide-rich phase melting point.

*The Tg was obscured by the lower melting endotherm.

EXAMPLE 4: PREFORMED STAPLE FORMATION

Staples were shaped and pointed in a manner which is similar to conventional metal staple forming. Only selected lengths of the polymeric wires of Example 2 were used for making preformed staples. The diameter of the chosen fiber lengths was limited to three sizes: 0.021, 0.018, and 0.015 inch (each size ±0.001 inch). The fiber was formed into a U-shape by bending it over a radius of approximately 0.010 inch to a 90° angle over a steel anvil at two bend points at room temperature with a pusher such that the backspan of the part was approximately 0.117 inch long. The minimal force to bend the fiber completely around the anvil without damaging it was applied. While the fiber was held against the anvil, each staple point was formed by shearing the fiber at a 45° angle to the long axis of the fiber with a steel cutting blade. The length of each leg of the staple was approximately 0.185 inch. The preformed staple was then released from the anvil. The staples were washed in a 1% solution of Pluronic F-68 (a nonionic surfactant) in water. They were then thoroughly rinsed in deionized water and methanol. The staples were dried at room temperature under vacuum to remove all water and methanol residues. The final preformed staple is shown in FIG. 1.

In its preformed state shown in FIG. 1, the surgical staple or staple blank 10 in accordance with the present invention is generally U-shaped as are conventional staples. The legs 14 are shown in parallel form, which is the conventional configuration for staples placed in a surgical stapler track. However, the surgical staple of this invention after being preformed (and before being placed in the stapler track) may relax such that the legs 14 are oblique to each other. Thus the staple 10 includes a back span 12, two legs 14, and an end point 16 formed at the extreme of each leg 14. The end points are sharply chiseled to cleanly pierce the body organs or tissue to be sutured. However, while the polymeric staple is deformable, the end points may be brittle and can break or crush if pressed against a hard surface.

Figure 2:
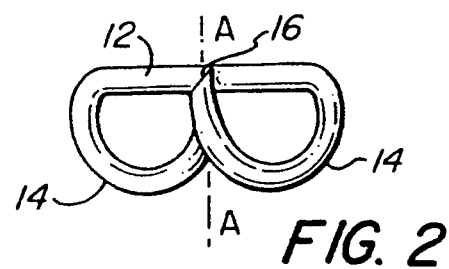
Figure 3:
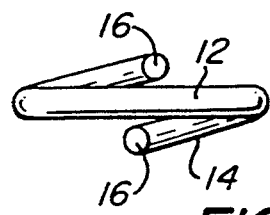
FIG. 3 is a top view of the deformed staple of FIG. 2.

FIGS. 2 and 3 show the staple 10 of FIG. 1 in its deformed state. As shown, the legs 14 are bent from their configuration perpendicular (they can also be oblique) to the back span 12 into an arcuate shape with the end points 16 extending toward opposite sides of the back span 12. Thus the brittle end points 16 do not encounter the underside of the back span 12 during deformation, and breaking or crushing of them is mitigated. Preferably, one end point 16 is guided toward one side of the back span and the other end point is guided toward the other side of the back span to further prevent the end points from engaging each other. The end points may desirably be closely adjacent opposite sides of the back span and may extend beyond or past the back span. The end points can also be bent so that each extends in an opposite direction across an axial plane A—A perpendicular to the back span 12 of the staple.

Figure 4:
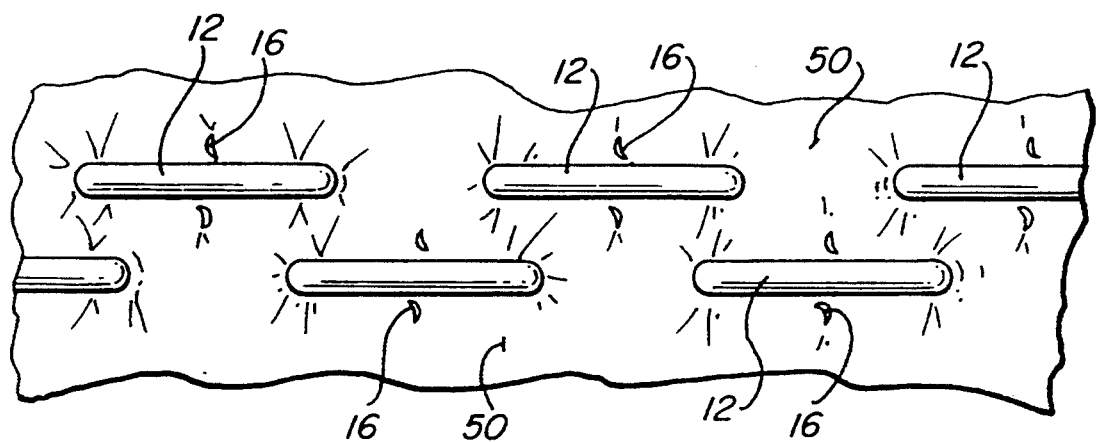
FIG. 4 is a top view showing the sequential in-vivo placement of the staple of FIG. 3.

As shown in FIG. 4, the end points 16 should be guided sufficiently close to the back span 12 so the stapled body organ 50 cannot work its way off of the end points.

EXAMPLE 5: STERILIZATION OF PREFORMED STAPLES: 5.a–c RADIATION STERILIZATION OF l-LAC/CAP FIBERS

In a dry environment, the polymeric staples formed from the fibers from Example 2, samples 1, 2 and 3 were packaged in predried paper support cards which were then inserted into foil laminate envelopes. The foil envelopes were heat sealed and packaged in Tyvek/Mylar outer pouches. The finished packages were sterilized via Cobalt 60 radiation at doses of 2.5 Mrad minimum to 3.0 Mrad maximum. The sterile staples from Example 2, samples 1, 2 and 3 were designated Examples 5.a, 5.b and 5.c respectively.

EXAMPLE 6: FORMATION AND TESTING OF FORMED STAPLES —STAPLE FORMATION

Figure 5:
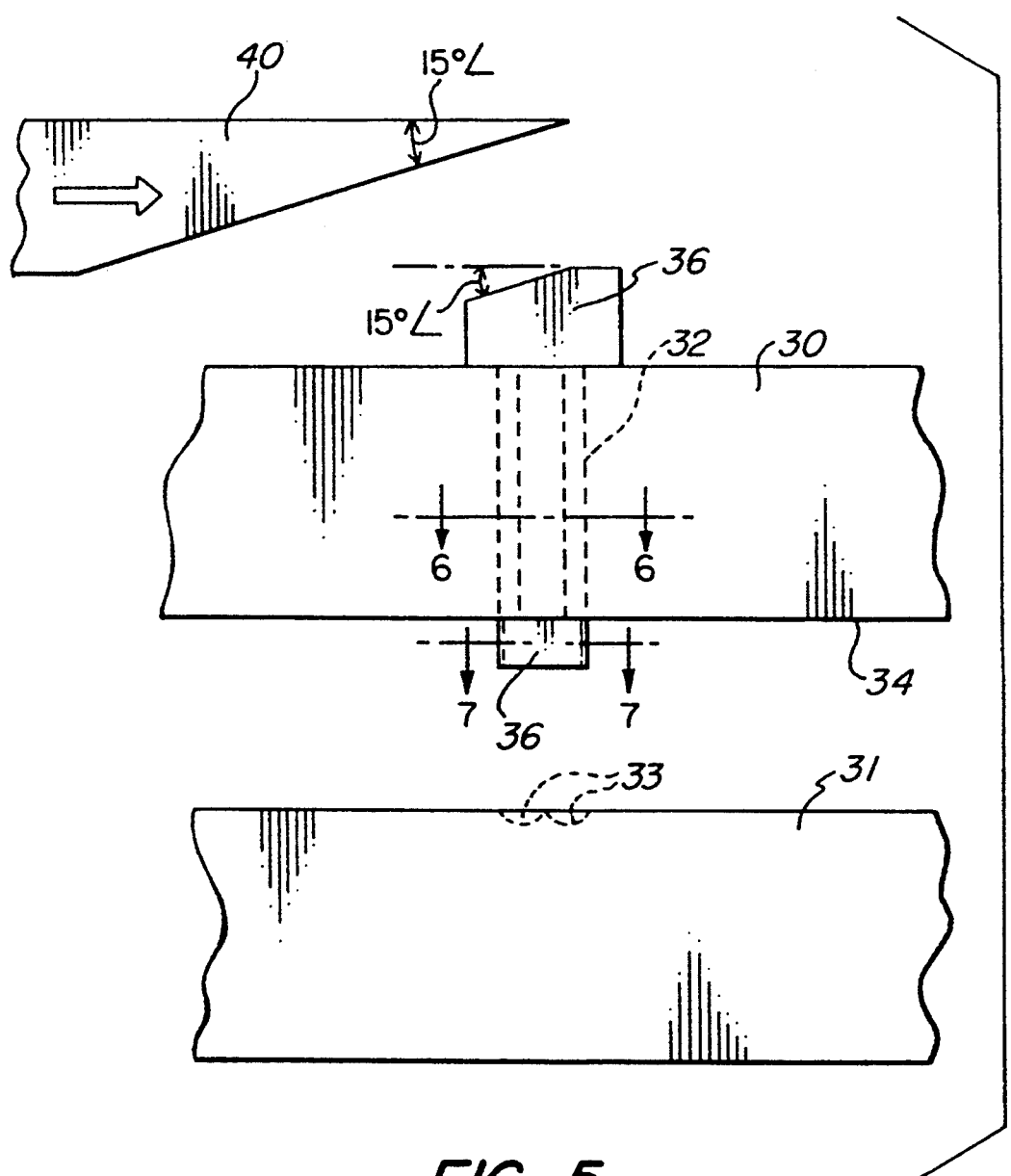
FIG. 5 is a partial side view showing apparatus for deforming the staple of FIG. 2.

The preformed staples of Example 4 could be implanted into various materials by using a delivery system which operated similarly to a metal stapler. Referring to FIG. 5, the delivery system consisted of two mating halves—a cartridge 30 and an anvil 31. Each preformed staple, as shown in FIG. 1, was loaded into a slot 32 in the cartridge such that the staple legs would be pushed against the anvil when the tool was activated. The anvil consisted of a number of specially designed pockets 33 which bent the staple legs as the staple was moved forward through the cartridge. The anvil pockets were designed so that the staple points, after passing through the pocket, would pass by the staple backspan on opposite sides. A single formed staple is shown in FIGS. 2, 3 and are described above.

The delivery device had a sufficient number of slots 32 and anvil pockets 33, FIG. 5, to form two rows of staples approximately 1 inch in length as shown in FIG. 4 and described above. Staple rows of this type are commonly used to suture parenchymal organs.

Figure 7:
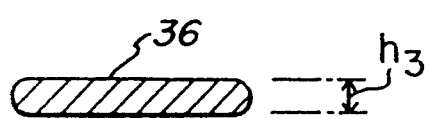
FIGS. 6 and 7 are partial cutaway views on the respective planes 6—6 and 7—7 of FIG. 5 showing slots and a pusher, respectively.
Figure 6:
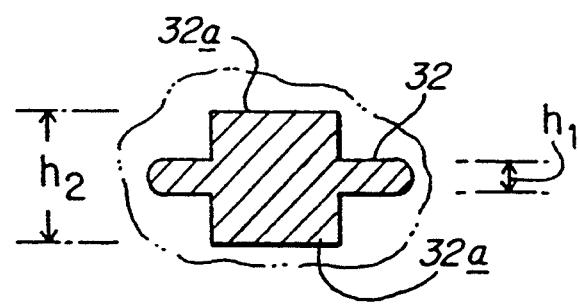

The gap between the bottom surface 34 of the cartridge 30 and the top surface of the anvil 31 was 0.040 in. The slot length (more fully shown in FIG. 6) was 0.166 in. Referring to FIG. 6, the slot extensions 32a accommodate the staple ends 16 (shown in FIGS. 2 and 3) if they pass over the top of the back span 12. The height $h_1$ is about 0.005 inches greater than the diameter of the chosen polymeric wire (see, e.g., Example 4 above). The height $h_2$ is approximately equal to three times $h_1$. Referring again to FIG. 5, the pusher 36 (more fully shown in FIG. 7) fits snugly into the slot and has a squared-off, flat end to provide uniform pressure across the back span 12 (shown in FIG. 1) of the staple 10 during the forming stroke. Referring to FIG. 7, the height $h_3$ is approximately equal to the diameter of the chosen polymeric wire described in Example 4 above. The length of the slot 32 and the pusher 36 (with the pusher length being about 0.005 inches less than the slot length) is approximately equal to the length of the back span 12, shown e.g. in FIG. 3.

At the completion of the staple formation stroke, the pusher 36 extended 0.010 in. beyond the slot opening 32 into the gap. A hand-actuated slide bar 40 was used to move the pusher 36 during the staple formation stroke form the final "B" shape of the staple.

Staple Opening Strength Testing

The opening strength of the staples was determined in the following manner. A single staple was loaded into the delivery system and formed through two layers of polyethylene (each 0.004 in T×1.0 in W ×5 in L). The staple was centered in the polyethylene strips and the backspan of the staple was perpendicular to the long axis of the strips. The same anvil pocket was used to form each staple. These specimens were tested before conditioning or after a specified in vitro conditioning period (7, 14, 21, 28, 35, or 42 days in 6.09 pH, 37±°0.2° C. buffer solution). The mechanical testing was performed using an Instron Testing Machine. The strength of each staple was determined by folding each polyethylene sheet back on itself and gripping the ends such that the two legs of the staple would open evenly when the Instron crosshead was activated. The maximum load recorded during the test was defined as the opening strength of the staple. The results of the mechanical testing are summarized in Table 4.

EXAMPLE 7: MOLDED PLAQUE OF l-LACTIDE-ε-CAPROLACTONE COPOLYMER

Polymer from Example 1.c was molded into a plaque for test specimen preparation using a heated hydraulic press. At a press temperature of 200° C., about 23 grams of dry polymer granules were pressed in a 4.25 inch by 4.25 inch by 0.062 inch steel frame between Teflon coated release liner fabric at 500 pounds of pressure for 4 minutes followed by a pressure increase to 5000 pounds for 4 minutes. The hot plaques, having the above-described dimensions of the steel frame, were cooled between chilled aluminum plates. The plaques were removed from the frame and annealed in the press at 100° C. and at about 250 pounds (14 psi) pressure for 5 minutes.

The material was found to undergo ductile deformation when bent at room temperature. The tensile properties were measured using ASTM method D638 on appropriate-sized bars cut out of the plaque. The modulus was 320,000 psi, the strength at yield was 6,300 psi. The elongation at yield was 3.4%. The strength at break was 5,100 psi, and the strain at break was 270%.

It is believed that a molded plaque of this type would be useful as a bone plate. One construction of a bone plate is shown in FIGS. 4–7 of U.S. Pat. No. 4,781,183, incorporated herein by reference.

EXAMPLE 8: GENERAL POLYMERIZATION PROCEDURE FOR l-LACTIDE/GLYCOLIDE-TRIMETHYLENE CARBONATE

TABLE 4

| | | Opening Strength (g) | | | | | | | | | | | |
|---|---|---|---|---|---|---|---|---|---|---|---|---|---|
| | | In Vitro Time (days) | | | | | | | | | | | |
| Ex. 2 | | 0 Days | | | 7 Days | | | 14 Days | | | 21 Days | | |
| Sample | Diam. (in) | n | Mean | S.D. | n | Mean | S.D. | n | Mean | S.D. | n | Mean | S.D. |
| 1 | 0.021 | 5 | 459 | 54.8 | 5 | 706 | 90.4 | 5 | 655 | 72.2 | 5 | 755 | 40.4 |
| 2 | 0.018 | 5 | 340 | 62.0 | 5 | 431 | 88.5 | 5 | 496 | 106.7 | 5 | 458 | 108.7 |
| 3 | 0.015 | 5 | 205 | 118.2 | 5 | 245 | 40.8 | 5 | 410 | 163.3 | 5 | 400 | 84.0 |
| 4 | 0.021 | 5 | 550 | 132.2 | 5 | 686 | 111.5 | 5 | 684 | 108.2 | 5 | 674 | 64.7 |
| 5 | 0.018 | 5 | 465 | 103.4 | 5 | 660 | 121.4 | 5 | 697 | 213.3 | 5 | 716 | 186.8 |
| 6 | 0.015 | 5 | 186 | 50.5 | 5 | 377 | 173.4 | 5 | 304 | 73.1 | 5 | 347 | 84.5 |

| | | In Vitro Time (days) | | | | | | | | |
|---|---|---|---|---|---|---|---|---|---|---|
| Ex. 2 | | 28 Days | | | 35 Days | | | 42 Days | | |
| Sample | Diam. (in) | n | Mean | S.D. | n | Mean | S.D. | n | Mean | S.D. |
| 1 | 0.021 | 5 | 760 | 102.3 | 5 | 751 | 72.8 | 5 | 713 | 74.2 |
| 2 | 0.018 | 5 | 557 | 189.7 | 5 | 564 | 90.2 | 5 | 574 | 126.6 |
| 3 | 0.015 | 5 | 214 | 20.3 | 5 | 346 | 186.3 | 5 | 221 | 99.2 |
| 4 | 0.021 | 5 | 782 | 85.7 | 5 | 780 | 110.5 | 5 | 755 | 135.5 |
| 5 | 0.018 | 5 | 703 | 96.6 | 5 | 718 | 308.2 | 5 | 850 | 212.9 |
| 6 | 0.015 | 5 | 319 | 91.3 | 5 | 317 | 42.5 | 5 | 383 | 162.7 |

| | | Staples Sterilized with 2.5 Mrad γ-irradiation | | | | | | | | | | | |
|---|---|---|---|---|---|---|---|---|---|---|---|---|---|
| | | In Vitro Time (days) | | | | | | | | | | | |
| Ex- | | 0 Days | | | 7 Days | | | 14 Days | | | 21 Days | | |
| ample | Diam. (in) | n | Mean | S.D. | n | Mean | S.D. | n | Mean | S.D. | n | Mean | S.D. |
| 5a | 0.021 | 5 | 524 | 44.6 | 5 | 600 | 48.6 | 5 | 627 | 56.5 | 5 | 601 | 49.9 |
| 5b | 0.018 | 5 | 283 | 48.2 | 4 | 361 | 91.2 | 5 | 356 | 66.2 | 5 | 319 | 66.6 |
| 5c | 0.015 | 5 | 153 | 13.4 | 5 | 162 | 38.2 | 5 | 192 | 27.1 | 5 | 226 | 50.9 |

| | | In Vitro Time (days) | | | | | | | | |
|---|---|---|---|---|---|---|---|---|---|---|
| Ex- | | 28 Days | | | 35 Days | | | 42 Days | | |
| ample | Diam. (in) | n | Mean | S.D. | n | Mean | S.D. | n | Mean | S.D. |
| 5a | 0.021 | 5 | 523 | 101.3 | 5 | 543 | 65.6 | 5 | 514 | 55.3 |
| 5b | 0.018 | 5 | 345 | 92.9 | 5 | 395 | 130.0 | 4 | 340 | 70.6 |
| 5c | 0.015 | 5 | 202 | 16.2 | 5 | 170 | 28.7 | 5 | 197 | 31.9 |

Trimethylene carbonate (TMC, 34.0 grams), diethylene glycol (DEG, 17.7 mg) and stannous octoate (20.2 mg) were combined and melted under a nitrogen atmosphere. The mixture was charged into a nitrogen purged stirred reactor at 200° C. The contents were stirred at this temperature for 25 minutes, at which point the mixture had obtained maximum melt viscosity. l-Lactide (l-Lac, 168.7 grams) and Glycolide (Gly, 18.7 grams) were melted and charged into the reactor. The contents were stirred at 200° C. for 2 hours at which point the mixture had again obtained maximum melt viscosity. The polymer was discharged from the reactor, ground, and dried in a vacuum oven at 100° C. and 0.2 mm Hg. The polymer had an inherent viscosity of 1.31 dl/g in chloroform, measured at 30° C. on a 0.5% solution. The polymer composition, as measured by $^1$H-NMR spectroscopy was 15.9/75.1/9.0 weight percent TMC/l-LAC/Gly.

EXAMPLE 9: MOLDED PLATE OF l-LACTIDE/GLYCOLIDE-TRIMETHYLENE CARBONATE

A plate having a thickness of 1 mm, a length of 35 mm and a width of 4.75 mm was formed from the polymer of Example 8 by injection molding. The mechanical properties are summarized in Table 5 before and after immersion in physiological saline solution at 37° C. for three and six weeks.

EXAMPLE 10: GENERAL POLYMERIZATION PROCEDURE FOR l-LACTIDE/GLYCOLIDE-ε-CAPROLACTONE

Caprolactone (Cap, 29.6 grams), diethylene glycol (DEG, 15.6 mg) and stannous octoate (17.9 mg) were combined and melted under a nitrogen atmosphere. The mixture was charged into a nitrogen purged stirred reactor at 200° C. The contents were stirred at this temperature for 45 minutes, at which point the mixture had obtained maximum melt viscosity.

TABLE 5

| Time (weeks) | Test | Plate Bending PLA/ PGA-TMC Plate | PLA/ PGA-CAP Plate |
|---|---|---|---|
| 0 | Bending Rigidity (lb/in) | 45.3 (±0.3) | 37.0 (±1.0) |
| 3 | | 40.9 (±2.2) | 36.2 (±1.3) |
| 6 | | 39.8 (±2.3) | 37.8 (±0.7) |
| 0 | Bending Strength (lbs/in) | 0.83 (±.02) | 0.64 (±.01) |
| 3 | | 0.53 (±.04) | 0.63 (±.02) |
| 6 | | 0.50 (±.05) | 0.65 (±.02) |
| 0 | Maximum Load (lbs) | 2.92 (±.02) | 2.15 (±.02) |
| 3 | | 2.14 (±.09) | 2.14 (±.06) |
| 6 | | 2.03 (±.10) | 2.20 (±.08) | l-Lactide (l-Lac, 153.3 grams) and Glycolide (Gly, 17.0 grams) were melted and charged into the reactor. The contents were stirred at 200° C. for 2 hours at which point the mixture had again obtained maximum melt viscosity. The polymer was discharged from the reactor, ground, and dried in a vacuum oven at 100° C. and 0.2 mm Hg. The polymer had in inherent viscosity of 1.40 dL/g in chloroform, measured at 30° C. on a 0.5% solution. The polymer composition, as measured by $^1$H-NMR spectroscopy was 15.9/74.1/10.0 weight percent CAP/l-LAC/Gly.

EXAMPLE 11: MOLDED PLATE OF l-LACTIDE/GLYCOLIDE E-CAPROLACTONE

A plate having a thickness of 1 mm, a length of 35 mm and a width of 4.75 mm was formed from the polymer of Example 10 by injection molding. The mechanical properties are summarized in Table 5 before and after immersion in physiological saline solution at 37° C. for three and six weeks.

Other embodiments will occur to those skilled in the art and are within the following claims.

What is claimed is:

1. A load-bearing, bioabsorbable surgical repair device comprising a tissue fixation device manufactured from a block copolymer having a hard and a soft phase, said hard phase of said copolymer having a plurality of first linkages consisting essentially of about 85 weight percent of the copolymer of lactic acid ester and said soft phase having a plurality of second linkages comprising about 15 weight percent of the copolymer of ε-caprolactone.

2. A load-bearing, bioabsorbable surgical repair device comprising a fracture fixation device manufactured from a block copolymer having a hard and a soft phase, said hard phase of said copolymer having a plurality of first linkages consisting essentially of about 85 weight percent of the copolymer of lactic acid ester and said soft phase having a plurality of second linkages comprising about 15 weight percent of the copolymer of ε-caprolactone.

3. A load-bearing, bioabsorbable surgical repair device comprising a tissue fixture device manufactured from a block copolymer having a hard and a soft phase, said hard phase of said copolymer having a plurality of first linkages consisting essentially of about 95 weight percent of the copolymer of lactic acid ester and said soft phase having a plurality of second linkages comprising about 5 weight percent ε-caprolactone.

4. A load-bearing bioabsorbable surgical repair device comprising a fracture fixation device manufactured from a block copolymer having a hard and a soft phase, said hard phase of said copolymer having a plurality of first linkages consisting essentially of about 95 weight percent of the copolymer of lactic acid ester and said soft phase having a plurality of second linkages comprising about 5 weight percent ε-caprolactone.

5. The device of claim 3 wherein said block copolymer is oriented in at least one direction.

6. A load-bearing, bioabsorbable surgical repair device comprising a tissue fixation device manufactured from a block copolymer having a hard and a soft phase, said hard phase of said copolymer having a plurality of first linkages consisting essentially of about 90 weight percent of said first linkages of lactic acid ester and about 10 weight percent of said first linkages of glycolic acid ester and said soft phase having a plurality of second linkages comprising about 15 weight percent of the copolymer of ε-caprolactone.

7. A load-bearing, bioabsorbable surgical repair device comprising a fracture fixation device manufactured from a block copolymer having a hard and a soft phase, said hard phase of said copolymer having a plurality of first linkages consisting essentially of about 90 weight percent of said first linkages of lactic acid ester and about 10 weight percent of said first linkages of glycolic acid ester and said soft phase having a plurality of second linkages comprising about 15 weight percent of the copolymer of ε-caprolactone.

8. A load-bearing, bioabsorbable surgical repair device comprising a tissue fixation device manufactured from a block copolymer having a hard and a soft phase, said hard phase of said copolymer having a plurality of first linkages consisting essentially of about 90 weight percent of said first linkages of lactic acid ester and about 10 weight percent of said first linkages of glycolic acid ester and said soft phase having a plurality of second linkages, comprising about 15 weight percent of the copolymer of trimethylene carbonate.

9. A load-bearing bioabsorbable surgical repair device comprising a fracture fixation device manufactured from a block copolymer having a hard and a soft phase, said hard phase of said copolymer having a plurality of first linkage consisting essentially of about 90 weight percent of said first linkages of lactic acid ester and about 10 weight percent of said first linkages of glycolic acid ester and said soft phase having a plurality of second linkages, comprising about 15 weight percent of the copolymer of trimethylene carbonate.

* * * * *